United States Patent [19]

Itoh et al.

[11] Patent Number: 5,086,127

[45] Date of Patent: Feb. 4, 1992

[54] SILICONE UV ABSORBERS CONTAINING SILANE UNITS

[75] Inventors: Kunio Itoh, Annaka; Mitsuo Umemura, Gunma; Eiichi Tabei, Kawasaki, all of Japan

[73] Assignee: Shin-Etsu Chemical Co., Ltd., Tokyo, Japan

[21] Appl. No.: 472,110

[22] Filed: Jan. 30, 1990

[30] Foreign Application Priority Data

Feb. 2, 1989 [JP] Japan .................................. 1-24246

[51] Int. Cl.$^5$ ...................... C08G 77/04; C08G 77/20; C08F 283/12; C08L 83/00
[52] U.S. Cl. ...................................... 525/474; 528/33; 528/32
[58] Field of Search ..................... 525/474; 528/10, 33, 528/32; 524/264, 265; 556/430; 522/6, 99

[56] References Cited

U.S. PATENT DOCUMENTS

| | | | |
|---|---|---|---|
| 4,590,253 | 5/1986 | Hasegawa et al. | 525/474 |
| 4,626,583 | 12/1986 | Arkles | 525/477 |
| 4,654,408 | 3/1987 | Okinoshima | 528/33 |
| 4,783,495 | 11/1988 | Pastor et al. | 524/265 |

*Primary Examiner*—Marion E. McCamish
*Assistant Examiner*—Susan Berman
*Attorney, Agent, or Firm*—Birch, Stewart, Kolasch & Birch

[57] ABSTRACT

Organic silicon compounds comprising in the molecule thereof, a polysilane structural unit: $-(R^1R^2Si)_n-$ and a structural unit: $R^3{}_aSiO_{(4-a)/2}$ absorb UV in the range of 300–400 nm and are well soluble in organic solvent. These compounds are useful UV absorbers for cosmetic compositions.

11 Claims, 3 Drawing Sheets

SILICONE UV ABSORBERS CONTAINING SILANE UNITS

The present invention relates to ultraviolet (UV) radiation absorbers useful in cosmetic and other compositions.

BACKGROUND OF THE INVENTION

Attention has been drawn to the deleterious effect of ultraviolet radiation on the skin in recent years. It is now recognized that exposure of the skin to excess ultraviolet radiation is harmful to health and beauty, because ultraviolet radiation not only causes wrinkles, but also invites pigmentation and skin aging to appear as freckles and spots and even induces skin cancers. To protect the skin from harmful ultraviolet radiation, a number of cosmetics having UV absorbers blended therein are now marketed.

There are known many UV which are useful in this application, including benzotriazole derivatives such as 2-(2-hydroxy-5-methylphenyl)benzotriazole, benzophenone derivatives such as 2-hydroxy-4-methoxybenzophenone, cinnamic acid derivatives such as 2-ethoxyethyl 4-methoxycinnamate, p-aminobenzoic acid derivatives, and salicylic acid derivatives. These UV absorbers, however, have problems including percutaneous absorption, skin irritation, solubility, and limited contents.

Inorganic pigments such as titanium oxide, zinc oxide and iron oxide, are also known as UV shielding agents to be blended in cosmetic compositions. Since these agents provide UV protection by scattering UV light rather than absorbing, their UV protection is insufficient. They shield visible light. They also have problems of skin irritation and toxicity.

Further, organopolysilanes having a silicon-to-silicon bond are known to be UV absorptive. Particularly for dimethylpolysilanes, it was reported that the longer the silicon chain to the longer wavelength side the absorption band is shifted. Most well-known dimethylpolysilanes have UV absorption bands at shorter wavelengths than 250 nm, but can not sufficiently absorb UV in the wavelength range of 290 nm or higher, which is believed to be harmful to the skin. Increasing the silicon chain results in a reduced solubility in organic solvents, a reduced blending in cosmetic compositions, and thus limited utilization.

The present invention is made to eliminate the above mentioned drawbacks, and its primary object is to provide a novel and improved UV absorber which is effective in absorbing UV rays having a wavelength of 290 nm or higher, less susceptible to percutaneous absorption, less irritative to the skin, and having the least amount of toxic.

SUMMARY OF THE INVENTION

According to the present invention, there is provided a UV absorber comprising an organic silicon compound containing in its molecule,
at least one polysilane structural unit of the formula:

$$-(R^1R^2Si)_n- \quad (1)$$

wherein $R^1$ is a substituted or unsubstituted alkyl radical having 1 to 10 carbon atoms, $R^2$ is a radical selected from the group consisting of substituted or unsubstituted alkyl radicals having 3 to 10 carbon atoms, cycloalkyl radicals having 5 to 10 carbon atoms, and aryl radicals having 6 to 10 carbon atoms, and letter n is an integer of 2 to 50, and
at least one structural unit of the formula:

$$R^3{}_aSiO_{(4-a)/2} \quad (2)$$

wherein $R^3$ is a radical selected from the group consisting of a hydrogen atom, a hydroxyl radical, a substituted or unsubstituted monovalent hydrocarbon radical having 1 to 10 carbon atoms, and $OR^4$ wherein $R^4$ is a substituted or unsubstituted monovalent hydrocarbon radical having 1 to 4 carbon atoms, and letter a is a positive number in the range of $0 < a \leq 4$.

Examining the UV absorption of various organopolysilanes, the present inventors have found that an organopolysilane comprising a structural unit (1) is effective in absorbing UV radiation in the wavelength range of from 300 to 400 nm, less susceptible to percutaneous absorption, and less irritative to the skin. The present inventors have modified the organopolysilane comprising a structural unit of formula (1) by bonding thereto an organopolysiloxane or alkoxysilane comprising a structural unit of formula (2), providing the organic silicon compound of the present invention which is well compatible with solvents so that it is a useful UV absorber to be blended in cosmetic and other compositions. The polysilane moiety of formula (1) is responsible for UV absorption while the moiety of formula (2) is responsible for solvent solubility.

BRIEF DESCRIPTION OF THE DRAWINGS

The above and other objects, features, and advantages of the present invention will be better understood from the following description.

DETAILED DESCRIPTION OF THE INVENTION

Figure 1:
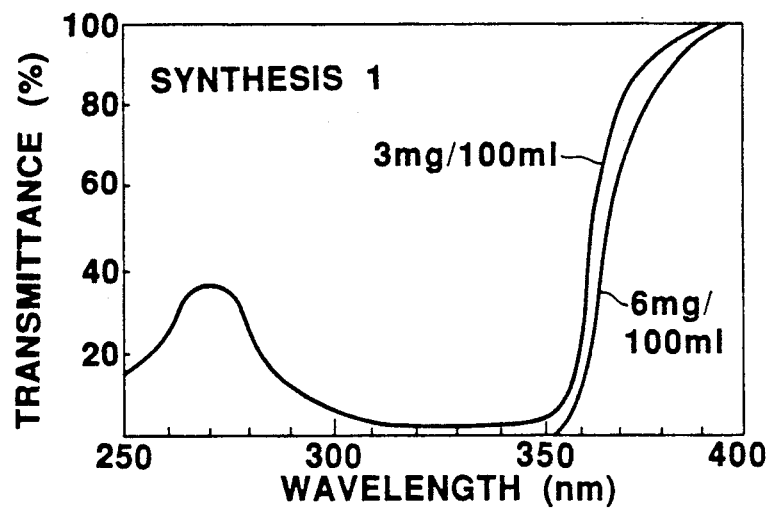
FIGS. 1 and 2 are UV absorption spectra of the UV absorbers of Syntheses 1 and 2, respectively.

The UV absorber of the present invention takes the form of an organic silicon compound comprising structural units of formulae (1) and (2) as defined above.

The first component is a polysilane structural unit of formula (1).

$$-(R^1R^2Si)_n- \quad (1)$$

In formula (1), $R^1$ is a substituted or unsubstituted alkyl radical having 1 to 10 carbon atoms, for example, a methyl, ethyl, propyl, butyl, pentyl, hexyl, heptyl, and octyl radical, with alkyl radicals having 3 to 10 carbon atoms being preferred. $R^2$ is a radical selected from the group consisting of substituted or unsubstituted alkyl radicals having at least 3 carbon atoms, preferably 3 to 10 carbon atoms, cycloalkyl radicals having 5 to 10 carbon atoms, and aryl radicals having 6 to 10 carbon atoms. Preferably $R^2$ is a phenyl radical. $R^1$ and $R^2$ may independently represent a substituted radical in which some or all hydrogen atoms attached to a carbon atom are replaced by halogen atoms, cyano or other radicals, for example, a trifluoropropyl radical. Letter n is an integer of at least 2, preferably 2 to 50, more preferably 5 to 50, most preferably 10 to 20.

The second component is a structural unit of formula (2).

$$R^3_a SiO_{(4-a)/2} \quad (2)$$

In formula (2), $R^3$ is a radical selected from the group consisting of a hydrogen atom, a hydroxyl radical, a substituted or unsubstituted monovalent hydrocarbon radical, and $OR^4$ wherein $R^4$ is a substituted or unsubstituted monovalent hydrocarbon radical having 1 to 4 carbon atoms, for example, alkyl radicals, alkenyl radicals, and alkoxy-substituted alkyl radicals. Examples of the hydrocarbon radical represented by $R^3$ include alkyl radicals having 1 to 10 carbon atoms, alkenyl radicals having 2 to 6 carbon atoms, and aryl radicals having 6 to 10 carbon atoms. Included are substituted radicals in which some or all hydrogen atoms attached to a carbon atom are replaced by halogen atoms, cyano or other radicals, for example, a trifluoropropyl radical. Letter a is a positive number in the range of $0 < a \leq 4$.

In the preferred compounds, siloxane unit (2) is present in greater molar amounts than polysilane unit (1). More preferably, there is present at least 2 mol, especially 2 to 3 mol of siloxane unit (2) per mol of polysilane unit (1).

Examples of the organopolysilane of the present invention are illustrated below.

$$X-(R^1R^2Si)_n-X \quad (i)$$

In the formula, $R^1$, $R^2$, and n are as defined above, and X is a hydrogen atom or a hydroxyl radical.

Although the compounds of formula (i) are outside the scope of the present invention, they are merely illustrated herein for convenience of description of the present invention.

In the formula, $R^1$, $R^2$, and n are as defined above; $R^5$ through $R^{13}$ are independently selected from the group consisting of alkyl radicals having 1 to 3 carbon atoms, alkenyl radicals having 2 to 6 carbon atoms, and aryl radicals having 6 to 10 carbon atoms; A is an alkylene radical having 1 to 6 carbon atoms; Y is selected from the group consisting of a hydrogen atom, a hydroxyl radical, alkyl radicals having 1 to 3 carbon atoms, alkenyl radicals having 2 to 6 carbon atoms, and aryl radicals having 6 to 10 carbon atoms; letters b and c are independently numbers of at least 1.

A typical example of the compound of formula (ii) is a compound of the formula:

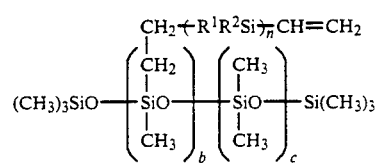

which is obtained by reacting a terminally vinyl functional polysilane: $CH_2=CH-(R^1R^2Si)_n-CH=CH_2$ with an SiH-containing polysiloxane:

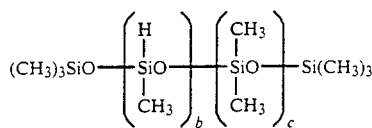

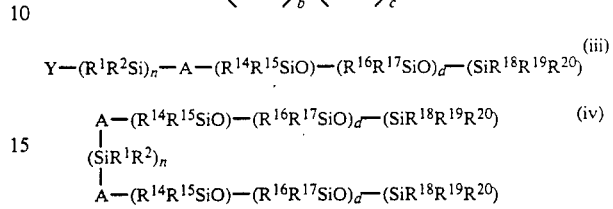

In formulae (iii) and (iv), $R^1$, $R^2$, A, Y, and n are as defined above; $R^{14}$ through $R^{20}$ are independently selected from the group consisting of alkyl radicals having 1 to 3 carbon atoms, alkenyl radicals having 2 to 6 carbon atoms, and aryl radicals having 6 to 10 carbon atoms, and letter d is a number of at least 1.

Typical examples of the compounds of formulae (iii) and (iv) include compounds of the formulae:

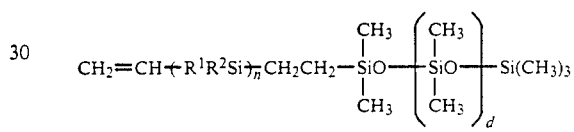

and

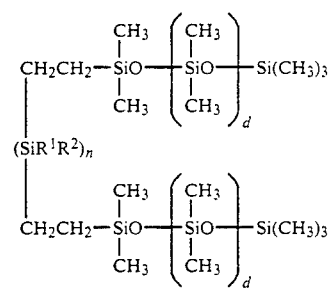

which are obtained by reacting a terminally vinyl functional polysilane: $CH_2=CH-(R^1R^2Si)_n-CH=CH_2$ with a single SiH-terminated polysiloxane:

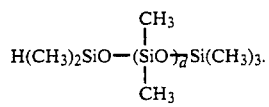

Also included is a compound of the formula:

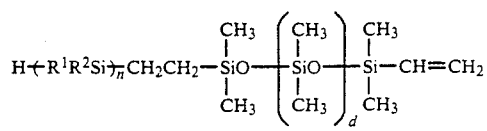

which is obtained by reacting an SiH-terminated polysilane: $H-(R^1R^2Si)_n-H$ with a terminally vinyl functional polysiloxane:

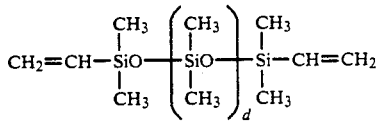

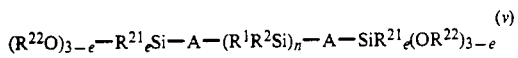

In formulae (v), $R^1$, $R^2$, A, and n are as defined above; $R^{21}$ is selected from the group consisting of alkyl radicals having 1 to 3 carbon atoms, alkenyl radicals having 2 to 6 carbon atoms, and aryl radicals having 6 to 10 carbon atoms, $R^{22}$ is selected from the group consisting of lower alkyl radicals having 1 to 4 carbon atoms and trialkylsilyl radicals in which the alkyl group has 1 to 4 carbon atoms, and letter e is equal to 0 or 1.

Typical examples of the compound of formula (v) are compounds of the formulae:

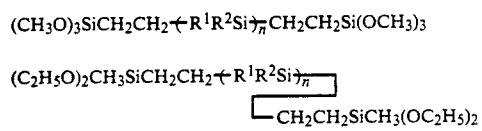

which are obtained by reacting a vinyl-terminated polysilane: $CH_2=CH-(R^1R^2Si)_n-CH=CH_2$ with an SiH-containing alkoxysilane such as $HSi(OCH_3)_3$ and $HCH_3Si(OC_2H_5)_2$.

Also included are compounds of the formulae:

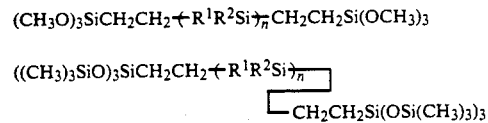

which are obtained by reacting an SiH-terminated polysilane: $H-(R^1R^2Si)_n-H$ with a vinyl alkoxysilane such as $CH_2=CHSi(OCH_3)_3$ and $CH_2=CHSi(OSi(CH_3)_3)_3$.

In formulae (ii) through (v), the alkylene radicals represented by A are preferably those having 1 to 3 carbon atoms, especially ethylene radicals, b is preferably in the range of from 1 to 10, especially from 1 to 5, and c and d each are preferably in the range of from 1 to 20, especially from 2 to 20.

In the above-mentioned compounds, it is an organopolysilane moiety of formula (1) that provides the UV absorbing effect intended herein whereas a structural unit moiety of formula (2) does not contribute to UV absorption, but imparts solvent solubility to the compounds. More illustratively, organopolysilanes of formula (i) are well soluble in aromatic solvents, but less soluble in aliphatic hydrocarbon solvents. They tend to gradually lower their solubility in the latter solvents as the silicon chain in formula (i) increases. Especially alkylphenylpolysilanes are least soluble in aliphatic hydrocarbons and dialkylpolysilanes become less soluble even in tetrahydrofuran as their silicon chain length increases. Therefore, as their silicon chain length is increased by increasing the value of n, the organopolysilanes of formula (i) increase and shift their maximum UV absorption toward a longer wavelength side, improving their overall UV absorptivity, but at the same time, lower their compatibility with solvents. By introducing a structural unit of formula (2), for example, by adding a siloxane chain through siloxane modification, the organopolysilanes of formula (i) can be improved in solvent solubility.

The organic silicon compounds comprising structural units of formulae (1) and (2) may be synthesized by any well-known method.

For example, polysilanes may be obtained by reacting an organochlorosilane with an alkali metal (M) in a suitable solvent such as toluene, xylene, and tetrahydrofuran as shown by the following schemes.

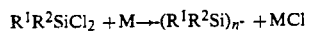

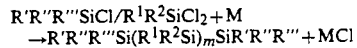

Either chain or three-dimensional polymers may be obtained through a proper choice of the number of chlorine atoms. A monochlorosilane serves as a chain terminator to regulate a degree of polymerization.

An alkenyl radical may be introduced, for example, by using a vinylchlorosilane as shown below.

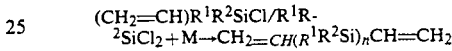

For the introduction of an SiH radical, a reaction mode as shown by the following scheme may be adopted.

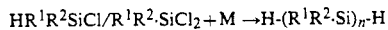

The thus obtained polysilanes are modified into the compounds of formula (ii) through (v) using any well-known method. It is preferred to use the addition reaction between $Si-CH=CH_2$ and Si-H as previously described. Also utilizable are co-hydrolysis between $Cl-(R^1R^2Si)_n-Cl$ and chlorosilane, and sodium-catalyzed condensation between $Cl-(R^1R^2Si)_n-Cl$ and $Cl-(R'R''Si-O)-SiR'R''Cl$.

The UV absorber of the invention may be composed of one or more of the organic silicon compounds mentioned above. Although the organopolysilanes comprising structural units of formula (1) are generally well soluble in aromatic solvents, among others, alkylphenylpolysilanes are less soluble in aliphatic solvents and dialkylpolysilanes tend to become less soluble even in tetrahydrofuran as their degree of polymerization increases. When it is desired to blend in cosmetic compositions, the compounds of formulae (ii) through (v) should be chosen for their compatibility with solvents.

The UV absorbers of the present invention may find a variety of applications in cosmetic compositions and other compositions requiring UV absorption. The amount of the UV absorber used may be suitably determined for a particular application without undue experimentation, for example, in the range of about 0.1 to 20% by weight, especially 1 to 10% by weight of the total weight of a cosmetic composition. A cosmetic composition for skin care, hair care and other purposes may be prepared in cream, liquid, emulsion and other forms by a conventional technique using any well known ingredients selected for a particular type of cosmetic composition.

The UV absorbers of the present invention can effectively absorb ultraviolet radiation in the wavelength range of from 300 to 400 nm. Percutaneous absorption, skin irritation, and toxicity problems are minimized.

Blending capability is improved. They are thus effective as UV absorbing ingredients in cosmetic and similar compositions.

EXAMPLE

Examples of the present invention are given below by way of illustration and not by way of limitation. All parts and percents are by weight unless otherwise stated.

EXAMPLE 1

Organopolysilanes terminated with ≡SiH at both ends and having a varying degree of polymerization (n) and organic radicals as shown in Table 1 were measured for maximum UV absorption wavelength (λmax) and coefficient of absorption (ε) using a spectrophotometer model U-3400 by Hitachi, Ltd. equipped with a 1-cm standard cell. The results are also reported in Table 1.

TABLE 1

| Polysilane | n | λmax (nm) | ε ($\times 10^3$) |
|---|---|---|---|
| Comparative Examples | | | |
| $(CH_3)_3SiSi(CH_3)_3$ | — | 194 | 10.8 |
| $CH_3((CH_3)_2Si)_nCH_3$ | 5 | 250 | 18.4 |
| $Ph(CH_3)_2SiSi(CH_3)_2Ph$ | — | 236 | 18.2 |
| Examples | | | |
| $-(Pr_2Si)_n-$ | 15 | 307 | 15 |
| $-(Bu_2Si)_n-$ | 65 | 313 | 370 |
| $-(Hex_2Si)_n-$ | 170 | 316 | 1400 |
| $-(Oct_2Si)_n-$ | 1870 | 317 | 1430 |
| $-(C-Hex.CH_3.Si)_n-$ | 146 | 321 | 582 |
| $-(CH_3PhSi)_n-$ | 97 | 338 | 977 |
| $-(C_2H_5PhSi)_n-$ | 8 | 333 | 35 |
| $-(PrPhSi)_n-$ | 14 | 328 | 46 |
| $-(BuPhSi)_n-$ | 14 | 337 | 160 |
| $-(HexPhSi)_n-$ | 25 | 339 | 170 |

Pr: propyl radical, Bu: butyl radical,
Hex: hexyl radical, C—Hex: cyclohexyl radical,
Oct: octyl radical, Ph: phenyl radical.

EXAMPLE 2

Synthesis 1

A 1-liter four-necked flask equipped with a mechanical stirrer, thermometer, condenser, dropping funnel, and nitrogen inlet tube was charged with 400 grams of toluene and 23 grams of metallic sodium pieces. The sodium was melted by heating in a nitrogen atmosphere. With vigorous stirring, 90 grams (0.47 mol) of methylphenyldichlorosilane was then added dropwise over one hour, and the contents were heated under reflux for a further 3 hours. The reaction mixture was cooled down, the solids were removed by filtration, and the solvent was removed from the filtrate. The residue was washed with a mixture of tetrahydrofuran and isopropanol, obtaining 29 grams (yield 52%) of a solid product having a number average molecular weight Mn of 11,000 as measured by gel permeation chromatography (GPC) and represented by $H-(CH_3C_6H_5Si)_{97}-H$.

Synthesis 2

In the same reactor as used in Synthesis 1, reaction was carried out in the same manner as in Synthesis 1 using 400 grams of toluene, 23 grams of metallic sodium pieces, 80 grams (0.42 mol) of methylphenyldichlorosilane, and 14.6 grams (0.08 mol) of methylphenylvinylchlorosilane. At the end of reaction, the reaction mixture was cooled down, the solids were removed by filtration, and the solvent was removed from the filtrate. The residue was washed with petroleum ether and acetone, obtaining 23 grams (yield 38%) of a semi-solid product having a number average molecular weight Mn of 1,850 as measured by GPC and represented by $CH_2=CH-(CH_3C_6H_5Si)_{15}-CH=CH_2$.

Next, 10 grams of the above-prepared organopolysilane was dissolved in 120 grams of toluene. After about 0.5 ml of a chloroplatinic acid-butanol catalyst (platinum 2% by weight) was added, the mixture was heated to 60° C. To the mixture was added dropwise 8.0 grams of

$H(CH_3)_2Si(OSi(CH_3)_2)_{18}OSi(CH_3)_3$ for reaction. There was obtained 15 grams (yield 83%) of a viscous product of the following formula.

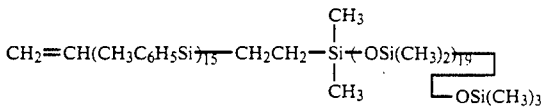

Figure 2:
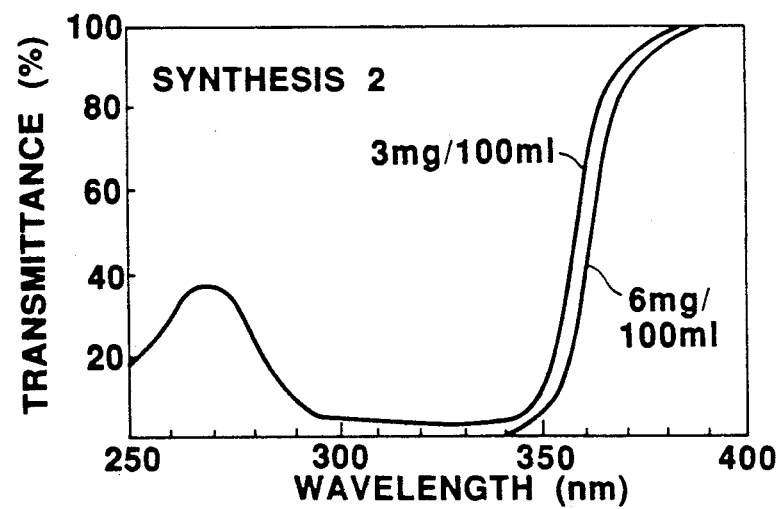

Next, the compounds of Syntheses 1 and 2 were dissolved in hexane in concentrations of 3 mg/100 ml and 6 mg/100 ml. These hexane solutions were measured for UV transmittance using a spectrophotometer model U-3400 by Hitachi, Ltd. equipped with a 1-cm standard cell. The results are plotted in FIG. 1 (Synthesis 1) and FIG. 2 (Synthesis 2).

For comparison purposes, commercially available UV absorbers were measured for UV transmittance. Samples included 25 mg/100 ml isopropyl alcohol solution of V Sorb 201, phenyl salicylate:

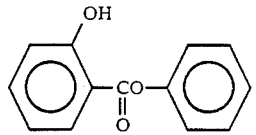

Figure 3:
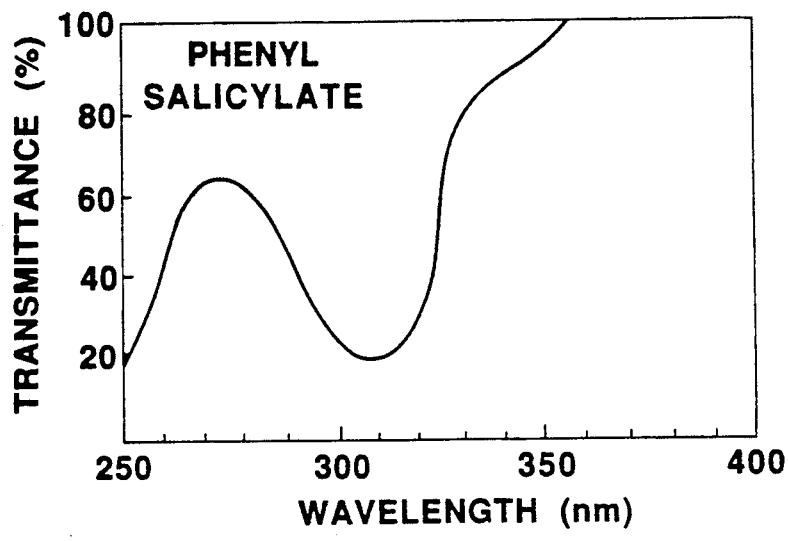
FIG. 3 is a UV absorption spectrum of phenyl salicylate.
Figure 4:
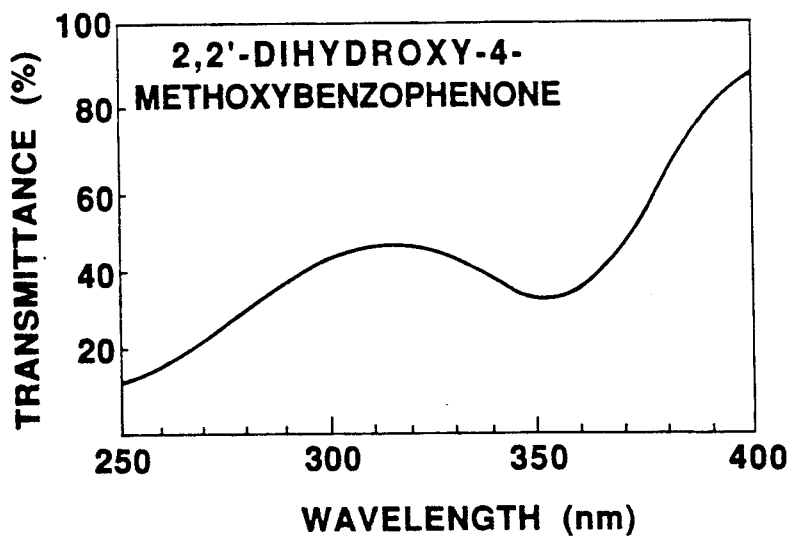
FIG. 4 is a UV absorption spectrum of 2,2'-dihydroxy-4-methoxybenzophenone.
Figure 5:
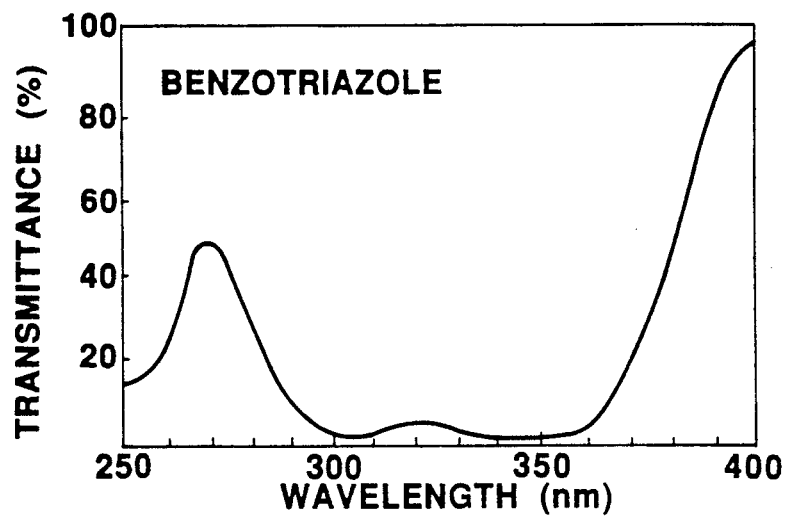
FIG. 5 is a UV absorption spectrum of a benzotriazole derivative.

5 mg/100 ml toluene solution of Cyasorb UV2, 2'-dihydroxy-4-methoxybenzophenone, and 5 mg/100 ml chloroform solution of Tinuvin 320, a benzotriazole derivative. The results are plotted in FIGS. 3, 4 and 5.

EXAMPLE 3

In the same reactor as used in Synthesis 1, reaction was carried out in the same manner as in Synthesis 1 using 400 grams of toluene, 23 grams of metallic sodium pieces, and 74 grams (0.4 mol) of di-n-propyldichlorosilane. The reaction mixture was cooled down, and the solids were removed by filtration. Methanol was added to the filtrate, causing a polymer to settle down. There was obtained 23 grams (yield 50%) of di-n-propylpolysilane having a number average molecular weight Mn of 2,000 as measured by GPC.

The polysilane was then blended in a cream of the composition shown in Table 2. Oil phase ingredients in the composition were agitated and mixed while heating at 70° C. The mixture was added to aqueous phase ingredients at 70° C. to form an emulsion, which was further emulsified by means of a homomixer. A cream product was obtained by allowing the emulsion to cool down with stirring.

TABLE 2

| | % by weight |
|---|---|
| Aqueous phase ingredients | |

TABLE 2-continued

| | % by weight |
|---|---|
| Purified water | 20 |
| Propylene glycol | 3 |
| Oil phase ingredients | |
| Microcrystalline wax | 8 |
| Paraffin | 2 |
| Bees wax | 2 |
| Vaseline | 3 |
| Hydrogenated lanolin | 9 |
| Squalane | 32 |
| Hexadecyl adipate | 6 |
| Glycerin monooleate | 4 |
| Polyoxyethylenesorbitan monooleate | 1 |
| Di-n-propylpolysilane | 1.6 |
| Octamethylcyclotetrasiloxane | 4 |
| Titanium oxide | 2.4 |
| Silica | 2 |

The cream was dispersed in ethanol in a concentration of 10% by weight before the dispersion was measured for UV transmittance. For comparison purposes, a commercially available sun-screen cream was dispersed in ethanol in a concentration of 10% by weight and measured for UV transmittance.

Figure 6:
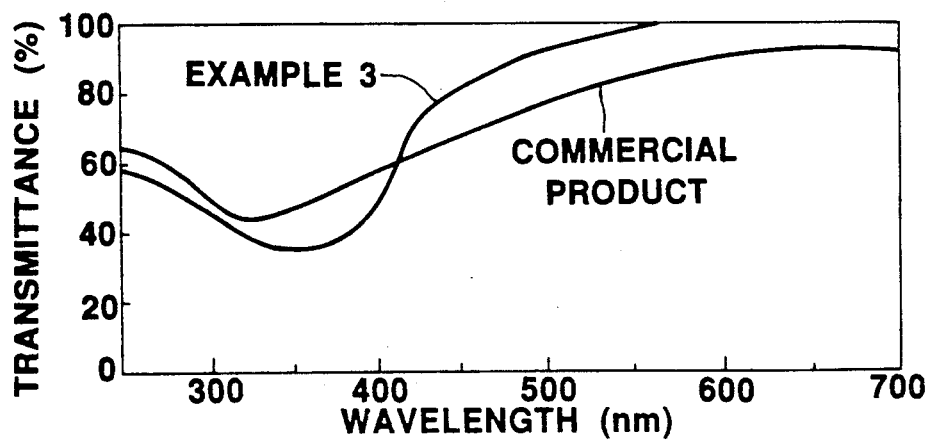
FIG. 6 show UV absorption spectra of a cream having a UV absorber of the present invention blended therein and a commercially available sun-screen cream.

The results are shown in FIG. 6. It is evident that the compound of Example 3 absorbs more UV in the wavelength range of 300 to 400 nm.

Although some preferred embodiments have been described, many modifications and variations may be made thereto in the light of the above teachings. It is therefore to be understood that within the scope of the appended claims, the invention may be practiced otherwise than as specifically described.

We claim:

1. A UV absorber comprising an organic silicon compound containing in its molecule
at least one polysilane structural unit of the formula:

$$—(R^1R^2Si)_n—  \quad (1)$$

wherein $R^1$ is a substituted or unsubstituted alkyl radical having 1 to 10 carbon atoms, $R^2$ is a radical selected from the group consisting of substituted or unsubstituted alkyl radicals having 3 to 10 carbon atoms, cycloalkyl radicals having 5 to 10 carbon atoms, and aryl radicals having 6 to 10 carbon atoms, and letter n is an integer of 5 to 50, and
at least one structural unit of the formula:

$$R^3{}_aSiO_{(4-a)/2} \quad (2)$$

wherein $R^3$ is a radical selected from the group consisting of a hydrogen atom, a hydroxyl radical, a substituted or unsubstituted monovalent hydrocarbon radical having 1 to 10 carbon atoms, and $OR^4$ wherein $R^4$ is a substituted or unsubstituted monovalent hydrocarbon radical having 1 to 4 carbon atoms, and letter a is a positive number in the range of $0 < a \leq 4$.

2. The UV absorber of claim 1 wherein said organic silicon compound is of the formula:

$$A—(R^1R^2Si)_n—Y \quad (ii)$$
$$(R^{11}R^{12}R^{13}SiO)—(R^5SiO)_b—(R^6R^7SiO)_c—(SiR^8R^9R^{10})$$

wherein $R^1$, $R^2$, and n are as defined above; $R^5$ through $R^{13}$ are independently selected from the group consisting of alkyl radicals having 1 to 3 carbon atoms, alkenyl radicals having 2 to 6 carbon atoms, and aryl radicals having 6 to 10 carbon atoms; A is an alkylene radical having 1 to 6 carbon atoms; Y is selected from the group consisting of a hydrogen atom, a hydroxyl radical, alkyl radicals having 1 to 3 carbon atoms, alkenyl radicals having 2 to 6 carbon atoms, and aryl radicals having 6 to 10 carbon atoms; letters b and c are independently numbers of at least 1.

3. The UV absorber of claim 1 wherein said organic silicon compound is of the formula:

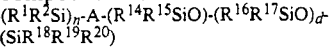
$$Y-(R^1R^2Si)_n-A-(R^{14}R^{15}SiO)-(R^{16}R^{17}SiO)_d-(SiR^{18}R^{19}R^{20})$$

wherein $R^1$, $R^2$, and n are as defined above; A is an alkylene radical having 1 to 6 carbon atoms; Y is selected from the group consisting of a hydrogen atom, a hydroxyl radical, alkyl radicals having 1 to 3 carbon atoms, alkenyl radicals having 2 to 6 carbon atoms, and aryl radicals having 6 to 10 carbon atoms; $R^{14}$ through $R^{20}$ are independently selected from the group consisting of alkyl radicals having 1 to 3 carbon atoms, alkenyl radicals having 2 to 6 carbon atoms, and aryl radicals having 6 to 10 carbon atoms; and letter d is a number of at least 1.

4. The UV absorber of claim 1 wherein said organic silicon compound is of the formula:

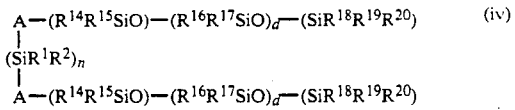
$$A—(R^{14}R^{15}SiO)—(R^{16}R^{17}SiO)_d—(SiR^{18}R^{19}R^{20}) \quad (iv)$$
$$|$$
$$(SiR^1R^2)_n$$
$$|$$
$$A—(R^{14}R^{15}SiO)—(R^{16}R^{17}SiO)_d—(SiR^{18}R^{19}R^{20})$$

wherein $R^1$, $R^2$, and n are as defined above; A is an alkylene radical having 1 to 6 carbon atoms; $R^{14}$ through $R^{20}$ are independently selected from the group consisting of alkyl radicals having 1 to 3 carbon atoms, alkenyl radicals having 2 to 6 carbon atoms, and aryl radicals having 6 to 10 carbon atoms; and letter d is a number of at least 1.

5. The UV absorber of claim 1 wherein said organic silicon compound is of the formula:

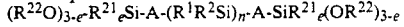
$$(R^{22}O)_{3-e}-R^{21}{}_eSi-A-(R^1R^2Si)_n-A-SiR^{21}{}_e(OR^{22})_{3-e}$$

wherein $R^1$, $R^2$, and n are as defined above; A is an alkylene radical having 1 to 6 carbon atoms; $R^{21}$ is selected from the group consisting of alkyl radicals having 1 to 3 carbon atoms, alkenyl radicals having 2 to 6 carbon atoms, and aryl radicals having 6 to 10 carbon atoms; $R^{22}$ is selected from the group consisting of lower alkyl radicals and trialkylsilyl radicals; and letter e is equal to 0 or 1.

6. The UV absorber of claim 1 wherein letter n of formula (1) is an integer of 10 to 20.

7. The UV absorber of claim 1 wherein the organic silicon compound is of the formula

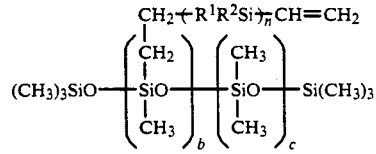
$$(CH_3)_3SiO—\left(\begin{array}{c}CH_2 \\ | \\ SiO \\ | \\ CH_3\end{array}\right)_b \left(\begin{array}{c}CH_3 \\ | \\ SiO \\ | \\ CH_3\end{array}\right)_c —Si(CH_3)_3$$

with $CH_2+R^1R^2Si+_n CH=CH_2$ attached wherein $R^1$, $R^2$, and n are as defined above; letters b and c are independently numbers of at least 1.

8. The UV absorber of claim 1 wherein the organic silicon compound is of the formula:

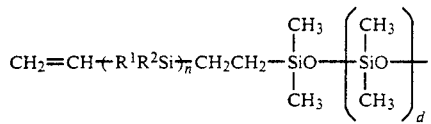

wherein $R^1$, $R^2$ and n are defined above; letter d is a number of at least 1.

9. The UV absorber of claim 1 wherein the organic silicon compound is of the formula:

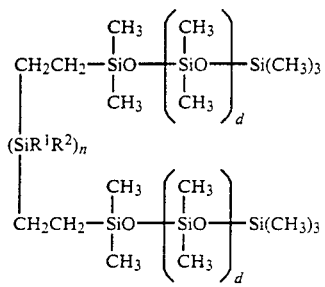

wherein $R^1$, $R^2$, and an are as defined above; letter d is a number of at least 1.

10. The UV absorber of claim 1 wherein the organic silicon compound is of the formula:

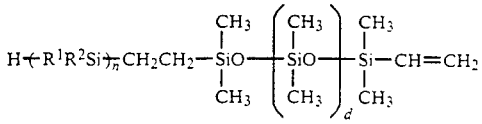

wherein $R^1$, $R^2$, and n are as defined above; letter d is a number of at least 1.

11. The UV absorber of claim 1 wherein the organic silicon compound is of the formula:

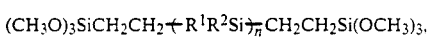

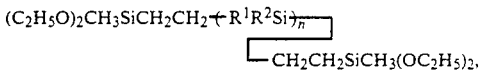

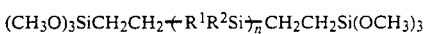

or

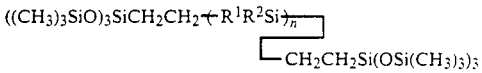

wherein $R^1$, $R^2$, and n are as defined above.

* * * * *